United States Patent

Engels et al.

[11] Patent Number: 5,166,330
[45] Date of Patent: Nov. 24, 1992

[54] PROCESS FOR THE PREPARATION OF NUCLEOSIDE ALKYL-ARALKYL- AND ARYL-PHOSPHONITES AND -PHOSPHONATES

[75] Inventors: Joachim Engels, Kronberg/Taunus, Fed. Rep. of Germany; Alfred Jäger, Charlottesville, Va.

[73] Assignee: Hoechst Aktiengesellschaft, Frankfurt am Main, Fed. Rep. of Germany

[21] Appl. No.: 139,112

[22] Filed: Dec. 28, 1987

Related U.S. Application Data

[63] Continuation of Ser. No. 647,473, Sep. 5, 1984, abandoned.

[30] Foreign Application Priority Data

Sep. 6, 1983 [DE] Fed. Rep. of Germany ....... 3332068

[51] Int. Cl.$^5$ .................. C07H 21/04; C07H 17/00; C07H 19/10; C07H 19/20
[52] U.S. Cl. .............................. 536/27; 536/28; 536/29
[58] Field of Search ..................... 536/27, 28, 29

[56] References Cited

U.S. PATENT DOCUMENTS

| | | | |
|---|---|---|---|
| 4,415,732 | 11/1983 | Caruthers et al. | 536/28 |
| 4,458,066 | 7/1984 | Caruthers et al. | 536/28 |
| 4,469,863 | 9/1984 | Ts'o et al. | 536/28 |
| 4,500,707 | 2/1985 | Caruthers et al. | 536/27 |
| 4,507,433 | 3/1985 | Miller et al. | 536/27 |
| 4,725,677 | 2/1988 | Koster et al. | 536/27 |
| 4,973,679 | 11/1990 | Caruthers et al. | 536/27 |

FOREIGN PATENT DOCUMENTS 0090789 10/1983 European Pat. Off.

OTHER PUBLICATIONS

Dorman et al., Tetrahedron, vol. 40, pp. 95-102, 1984.
Sinha et al., Tetrahedron Letters 24(9): 877-880, 1983.
Jager et al., Tetrahedron Letters 25(14): 1937-1442, 1984.
McBride et al., Tetrahedron Letters 24(3): 245-248, 1983.
Engels et al., Angew Chem. Suppl. pp. 2010-2015, 1982.
Sinha et al., Tetrahedron Letters 24(4): 877-880, 1983.
Agarwal et al., Nucl. Acids Res. 6(9): 3009-3024, 1979.
Nemer et al., Tetrahedron Letters 21: 4149-4152, 1980.
Burgers et al., Tetrahedron Letters, 40: 3835-3838, 1978.
Miller et al., Biochemistry 18(23): 5134-5143, 1979.
Methoden der Organishen Chemie XII(1):324-328 and 334-336 (1963).
Organishche Phosphorverbindungen I:285-286, 291 and 294-296 (1982).
McBride et al., Tetrahedron Letters, 24(3), pp. 245-248 (1983).
Engels et al., Eine Neue Synthese von Nukleosidmethylphosphonaten, Angew Chem Suppl, 2010-2015 (1982).
Sinha et al., A New Synthesis of Oligodeoxynucleoside Methylphosphonates on . . . Glass . . . Support Using Phosphite Approach, Tetrahedron Letters 24(9), 877-80 (1983).
Agarwal et al., Synthesis . . . of Deoxyribooligonucleotides Containing Methyl and Pherylphosphonate Linkages, Nucleic Acids Research 6(9), 3009-3024 (1979).
Nemer et al., Ribonucleotide Analogues Having Novel Internucleotide Linkages, Tetrahedron Letters 21, 4149-52 (1980).
Burgers et al., Synthesis of Dinucleoside Monophosphorothioates via Addition of Sulphur to Phosphite Triesters, Tetrahedron Letters 40, 3835-38 (1978).
Miller et al., Nonionic Nucleic Acid Analogues, Synthesis and Characterization of Dideoxyribonucleoside Methylphosphonates, Biochemistry 18(23) 5134-43 (1979).

*Primary Examiner*—Johnnie R. Brown
*Assistant Examiner*—Gary L. Kunz
*Attorney, Agent, or Firm*—Finnegan, Henderson, Farabow, Garrett and Dunner

[57] ABSTRACT

Deoxyribonucleoside phosphonates, thiophosphonates and selenophosphonates are obtained by condensation of a difunctional phosphonylating reagent of the formula

R—PXY, in which R is an inert non-cytotoxic organic radical, X is chlorine or Y and Y is a secondary amino group, with a deoxyribonucleoside of which the 5-hydroxyl group and any exo-amino group presents in the base radical are protected, and further condensation with a nucleoside of which the 3-hydroxyl group and any exo-amino group present in the base radical are protected, and then oxidation. The thiophosphonates and selenophosphonates and the intermediates of the first condensation stage are new.

11 Claims, No Drawings

PROCESS FOR THE PREPARATION OF NUCLEOSIDE ALKYL-ARALKYL- AND ARYL-PHOSPHONITES AND -PHOSPHONATES

This application is a continuation of application Ser. No. 647,473, filed Sep. 5, 1984, now abandoned.

Non-ionic analogs of deoxyribonucleic acids (DNA) are important for the investigation of DNA-DNA and DNA-protein interactions. Of particular interest are phosphonic acid esters of deoxyribonucleotides as a result of their chemical stability and on the basis of their capability to enter into cells and their high resistance to cell nucleases. Hitherto, four different strategies have been described for the synthesis of methylphosphonate analogs of nucleotides:

1. Ogilvie et al. (M. J. Nemer and K. K. Ogilvie, Tetrahedron Lett. 21, Page 4149 (1980)) prepared a completely protected uridyl-3',5'-uridine methylphosphonate by Michaelis-Arbuzov rearrangement of the corresponding phosphite intermediates. This reaction (methyl iodide, 20 hours at 50° C.) might not be generally applicable as a result of its drastic conditions, because, for example, methylation of the purine bases is to be expected.

2. Ts'o et al. (P. S. Miller, J. Yano, E. Yano, C. Caroll, K. Jayaraman and P.O.P. Ts'o, Biochemistry 18, 5134 (1979); Proc. Natl. Acad. Sci. USA 78, 1537 (1981); P. S. Miller, N. Drean, S. M. Pulford and K. B. McParland, J. Biol. Chem. 225, 9659 (1980)) developed a synthesis strategy which is analogous to the phosphotriester method in oligonucleotide synthesis. Here, a protected nucleotide 3'-O-methylphosphonic acid β-cyanoethyl ester is used as the most important intermediate. This method has the known advantages and disadvantages of the phosphotriester method, the low reactivity of the phosphorus(V) compound being mentioned in particular as a disadvantage.

3. Agarwal et al. (K. L. Agarwal and F. Riftina, Nucl. Acid Res. 6, 3009 (1979)) used methylphosphonic acid dichloride as a difunctional phosphonylating agent. In the second step, the chloride has to be activated by means of tetrazole. The crude product obtained can only be purified by efficient chromatography.

4. J. Engels and A. Jäger, Angew. Chem. Suppl. 1982, 2010, and N. D. Sinha, V. Grossbruchhaus and H. Köster, Tetrahedron Lett. 24, 887 (1983) used methyldichlorophosphane as the starting material. The latter authors synthesized the nucleotide methylphosphonates on a polymeric support. The products obtained are yet to be characterized.

Whereas the reactivity of the second halogen of methylphosphonic acid dichloride is generally too low and additional activation is necessary, the activity in the case of phosphinic acid dichlorides is if anything too high. Thus, handling difficulties arise (extremely anhydrous medium) and, in addition, the symmetrical phosphonous acid ester is unavoidably formed.

By contrast, the invention relates to a process for the preparation of deoxyribonucleoside phosphonates of the general formula I

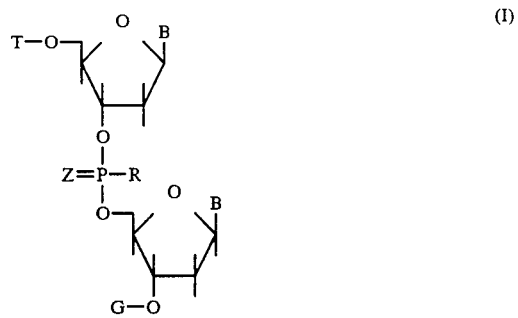

in which

T denotes a protecting group for a primary hydroxyl group, preferably triphenylmethyl (=Tr), p-anisoyldiphenylmethyl or di(p-anisoyl)phenylmethyl, B denotes a nucleoside base radical in which any exoamino group present is protected, preferably 1-thyminyl, 1-(N-4-benzoylcytosinyl), 9-(N-6-benzoyladeninyl) or 9-(N-2-isobutyroylguaninyl), G denotes a protecting group for a secondary hydroxyl group, Z denotes oxygen, sulfur or selenium and R denotes alkyl having up to 8 C atoms, cyclohexyl, benzyl, or phenyl optionally substituted by fluorine, chlorine, bromine, lower alkyl, lower alkoxy or trifluoromethyl, and preferably denotes methyl, ethyl, phenyl or benzyl, especially methyl, wherein a difunctional phosphonylating reagent of the general formula II

wherein X denotes chlorine or Y and Y denotes a group of the formula

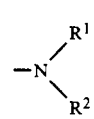

$R^1$ and $R^2$ representing identical or different alkyl or cycloalkyl radicals having up to 8 C atoms, or phenyl radicals, or $R^1$ and $R^2$, together with the nitrogen, representing a saturated or unsaturated heterocyclic ring which can contain further heteroatoms, is reacted with a nucleoside of the general formula III

wherein T and B have the meanings given above, preferably at −80° to +100° C., in particular at −20° to 0° C., the resulting compound of the general formula IV

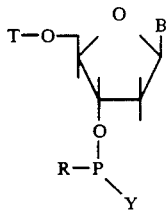

(IV)

is reacted with a compound of the general formula V

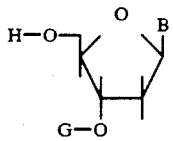

(V)

wherein B and G have the meanings given above, preferably at −20° to +100° C., in particular at room temperature, and the resulting compound of the general formula VI

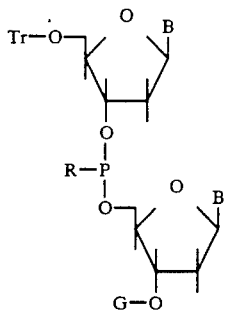

(VI)

wherein T, R, B and G have the meanings given above, is oxidatively converted to compounds of the general formula I, preferably at −80° to +100° C., in particular at −20° C. to room temperature.

The compounds of the general formula I in which Z denotes sulfur or selenium, and the intermediates of the general formula IV, are new and also form a subject of the invention.

In principle, the radical R in the difunctional phosphonylating reagent of the general formula II can be any non-cytotoxic organic radical which is inert towards the compounds of the general formulae II to VI and which does not hinder the reactions.

Examples of possible groups of the general formula —NR$^1$R$^2$ are: dimethylamino, diethylamino, diisopropylamino, methylethylamino, methylpropylamino, methylhexylamino, methylcyclohexylamino, methylbenzylamino, morpholino, pyrrolidino, piperidino, methylanilino, diphenylamino, imidazolo, triazolo, benzotriazolo and tetrazolo.

The starting materials of the general formula II in which X denoted chlorine can be obtained by reacting the corresponding dichlorophosphane, preferably methyldichlorophosphane, with a secondary amine of the general formula VII

H—NR$^1$R$^2$ (VII)

in which R$^1$ and R$^2$ have the meanings given above. Correspondingly, compounds of the general formula II in which X denotes a group of the formula Y are accessible by further reaction with the same secondary amine or a different secondary amine of the general formula VII. The compounds of the formula II can be purified by vacuum distillation.

The reaction of the phosphonylating reagent of the general formula II with a suitably protected nucleoside of the general formula III is carried out in a moderately polar solvent, preferably chloroform, with the exclusion of moisture. Tertiary amines, preferably ethyldiisopropylamine (Hünig's base), can be used as auxiliary bases for this reaction. Working-up is carried out by aqueous extraction and precipitation of the products of the general formula IV with a non-polar solvent such as petroleum ether or pentane. The phosphonous acid ester-amides of the general formula IV obtained in this way precipitate as colorless powders and can be characterized by spectroscopic data such as $^1$H—NMR, $^{31}$P—NMR or UV and elementary analysis. Furthermore, they can also be converted, by direct oxidation, to the phosphonic acid ester-amides of the general formula VIII

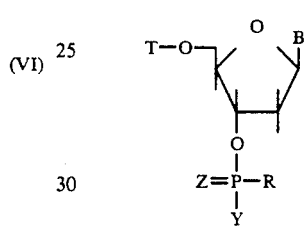

(VIII)

T, B, Z, R and Y having the meanings given above, which can then be isolated and characterized.

Remarkably, no symmetrical dinucleoside 3′,3′-phosphonite is formed within the limit of detection.

As shown by $^{31}$P-NMR, the compounds of the general formula IV are stable for at least 1 month in powder form, when stored dry and at a maximum of −20° C. This great stability of the phosphonous acid esteramides is astonishing and emphasizes the value of this method. Its universal applicability in the synthesis of phosphonic acid diesters of nucleosides is shown by the reaction with suitably 3′-protected nucleosides:

In this reaction, the 5′-protected nucleoside phosphonites of the general formula IV are dissolved in a moderately polar solvent, preferably acetonitrile, chloroform or tetrahydrofuran, and mixed with the nucleoside of the general formula V (protected in the 3′-position). Suitable protecting groups G in the compounds of the general formula V are acyl groups such as benzoyl, acetyl, pivaloyl or levulonyl, or silyl groups such as t-butyldimethylsilyl. The reaction is catalyzed by an acid, preferably an azole or amine hydrochloride. Benzotriazole is particularly suitable. It is remarkable that HPLC analysis of the product shows no symmetrical 5′,5′-isomer and only traces of the 3′,3′-isomeric phosphonate.

The labile intermediate, namely the phosphonous acid triester of the general formula VI, is oxidized directly to the phosphonate of the general formula I. In addition to the oxidizing agents usually employed for this purpose, such as dinitrogen tetroxide or iodine, peroxides, in particular anhydrous t-butyl hydroperoxide, have proved valuable. The reaction is preferably carried out in a moderately polar solvent, particular preference being afforded to acetonitrile or chloroform.

Particular consideration should be given to the known acid-catalyzed transesterification of the diacylalkylphosphonites (F. W. Hoffmann, R. G. Roth and T. C. Simmons, J. Amer. Chem. Soc. 80, 5937–40 (1958)).

The compounds (some of which are already known) are characterized by means of $^{31}$P-NMR and $^1$H-NMR and also chromatographic comparisons with authentic material.

The compounds of the general formula I in which Z denotes sulfur or selenium are prepared by direct reaction of the compounds of the general formula VI with elemental sulfur or selenium. Stirring with the stoichiometric quantity of sulfur or selenium, in a polar solvent such as tetrahydrofuran, leads to good yields of the corresponding thiophosphonates or selenophosphonates of the general formula I. Characterization is carried out by means of $^{31}$P-NMR and $^1$H-NMR as well as elementary analysis.

Because of the presence of a center of asymmetry in the nucleoside moiety and the production of another on the phosphorus, the phosphates of the general formula I exist as mixtures of diastereomers (see Table 6, isomers 1 and 2).

The isomer ratio, which is close to the statistical ratio of 1:1, is only very slightly influenced by a variation in the parameters such as the solvent, the temperature and the sequence of addition.

The examples which follow describe the invention in greater detail:

EXAMPLE 1

Starting material $H_3C$-$P[N(CH_3)_2]_2$

In a 1000 ml three-necked flask fitted with a dropping funnel and a mechanical stirrer, 125 ml (1.9 mol) of dimethylamine are introduced into 400 ml of anhydrous diethyl ether and reacted, over a period of 60 minutes, with a solution of 60 ml (0.40 mol) of methyldichlorophosphane in 200 ml of anhydrous ether, while cooling with ice. After stirring for 2 hours at room temperature and for 1 hour at 50° C., the precipitate is filtered off under a protective gas and rinsed twice with 100 ml of ether and the filtrate is concentrated at about 0.1 bar. The remaining residue is rapidly distilled over at 0.5 bar/124° C. Precision distillation with a Vigreux column (50 cm) at 64°–65° C./65 mbar gives 36.6 g (66% of theory) of a colorless liquid.

| Analysis: $Cl^{(-)} < 0.2\%$ | |
|---|---|
| $^{31}$P-NMR (THF) | $\delta = 87$ ppm |
| $^1$H-NMR (CDCl$_3$) | $\delta = 1.23$ ppm (d, 7Hz, P—CH$_3$) |
| | $\delta = 2.66$ ppm (d, 7Hz, N(CH$_3$)$_2$) |

EXAMPLE 2

The 5'-tritylnucleosides III (1 mmol) are dissolved in 6 ml of anhydrous chloroform under an inert nitrogen atmosphere and $H_3CP[N(CH_3)_2]_2$ (2 mmol) is added. The reaction is complete after 12 hours at room temperature (stirring) or after only 2 hours if catalytic quantities (0.1 mmol) of collidine hydrochloride are added.

The solution is then transferred with 100 ml of methylene chloride to a 250 ml separating funnel and extracted twice by shaking with 50 ml of saturated sodium chloride solution (containing 0.1 ml of triethylamine). The organic phase is dried over anhydrous sodium sulfate and concentrated to a foam. This is stirred for 2 hours with 50 ml of pentane. The residue is filtered off and dissolved in 2 ml of diethyl ether and the solution is slowly added dropwise to 50 ml of thoroughly stirred pentane. The fine precipitate is filtered off and dried to give an 85-95% yield of the compound of the general formula IV (Tables 2 and 3).

The compounds can be identified directly by $^{31}$P nuclear magnetic resonance spectroscopy or, after oxidation with t-butyl hydroperoxide, as phosphonic acid ester-amides of the general formula VIII (Tables 4 and 5).

In the $^{31}$P-NMR spectrum, these substances show up to 3% of hydrolyzed product (nucleoside methylphosphinate), but no detectable quantity of symmetrical dinucleoside 3',3'-phosphonite. This demonstrates the superiority of the method compared with former methods, which always yielded about 5-10% of these products. When stored as dry powders at −20° C., no decomposition can be observed within a month.

The following reagents were also employed analogously:

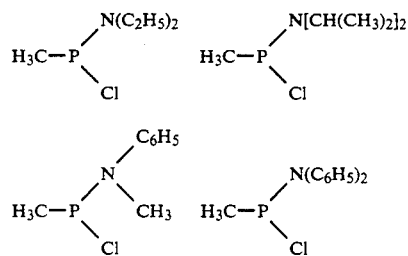

EXAMPLE 3

The 5'-tritylnucleoside III (1.00 mmol) and 1.71 ml (10 mmol) of N,N,N-ethyldiisopropylamine are introduced into 6 ml of THF, and 2.00 mmol of phosphonylating agent II are then slowly added dropwise. After stirring at room temperature overnight, the reaction solution is added dropwise to ice-cold water (50 ml, saturated with NaCl). After extraction with twice 20 ml of methylene chloride, the organic phase is dried with sodium sulfate and the solvent is removed in vacuo. Further purification is carried out by precipitation as above (Tables 2 and 3).

EXAMPLE 4

3'-O-Benzoylthymidine (0.20 mmol) and 1-H-benzotriazole (0.80 mmol) are dried in a round-bottomed flask and then dissolved in 1.0 ml of dry acetonitrile. The reaction is complete within one minute, a very air-labile and acid-labile phosphonite VI being formed; this is converted directly to the phosphonates I, with 80–90% yield, by oxidation with anhydrous t-butyl hydroperoxide (0.25 mmol) (according to H. Langhals, E. Fritz and J. Mergelsberg, Chem. Ber. 113, 3662 (1980)) dissolved in acetonitrile or tetrahydrofuran.

Alternatively, 30 mg (0.95 mmol) of sulfur are added to 0.7 mmol of VI at −20° C. and the mixture is stirred overnight at room temperature. The reaction is generally already complete after a few hours. 20 ml of chloroform are then added and the organic phase is extracted three times by shaking with water. After drying over sodium sulfate and removal of the solvent, a crude product is obtained which is purified by silica gel chromatography to give the compound I in 80–90% yield (Table 6).

Alternatively, 118 mg (1.5 mmol) of black selenium are added to 0.7 mmol of VI and the mixture is stirred overnight. After working-up (as above), the compound I is obtained in 60% yield (Table 6).

HPLC analysis of the reaction mixture (in the case where Z=O by comparison with the authentic reference, P.O.P. T'so et al., Biochemistry 18, 5134 (1979)) showed about 1% of the 3',3'-phosphonates and no 5',5'-isomer.

TABLE 1

Compounds (II)

H₃C—PXY

| X | Y | $^{31}$P-NMR δ(ppm)$^{a)}$ | B.p. °C./bar | $^1$H-NMR (CDCl$_3$), δ(ppm) P—CH$_3$ | Other protons |
|---|---|---|---|---|---|
| —Cl | —N(CH$_3$)(C$_6$H$_5$) | $-141.2^{b)}$ | 55–47/10$^{-8}$ | 1.61 d(J=13.1Hz) | 7.41–7.18  3.20 (m, 5H, aromatic H, d (J=8.3Hz)) |
| —Cl | —N(C$_6$H$_5$)$_2$ | $-132.2^{b)}$ | 92–44/10$^{-8}$ | 1.53 d(J=14Hz) | 7.5–6.9 (m, 10H, aromatic H) |
| —N(imidazolyl) | —N(imidazolyl) | $-62^{c)}$ | 92/10$^{-5}$ (M.p.: 60° C.) | 2.20 d(J=10Hz) | 7.45(s, 2H) 6.95(s, 4H) |
| —N(1,2,4-triazolyl) | —N(1,2,4-triazolyl) | $-72^{c)}$ | (M.p.: 110° C.) | 2.32 d(J=9Hz) | 8.51(s, 2H) 8.07(s, 2H) |
| —N(nitrotriazolyl) | —N(nitrotriazolyl) | $-91^{c)}$ | — | 2.49 d(J=9Hz) | 8.89(s, 2H) |
| —N(tetrazolyl) | —N(tetrazolyl) | $-81^{d)}$ | | 2.60 d(J=9Hz) | 8.88(s, 2H) |

$^{a)}$relative to 85% H$_3$PO$_4$
$^{b)}$1,2-dichloroethane
$^{c)}$THF
$^{d)}$dioxane

TABLE 2

Compounds (IV)

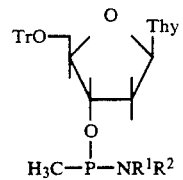

| R$^1$ | R$^2$ | $^{31}$P-NMR, δ(ppm)$^{a)}$ (1,2-dichloroethane) | H-6 | CH$_3$ | P—CH$_3$ | NR$^1$R$^2$ |
|---|---|---|---|---|---|---|
| CH$_3$ | CH$_3$ | −139.6/140.7 | 7.60/7.57 (s) | 1.44/1.43 d(J=1.2Hz) | 1.16/1.14 d(J=7.3/7.0Hz) | 2.76/2.47 d(J=8.9Hz), N(CH$_3$)$_2$ |
| C$_2$H$_5$ | C$_2$H$_5$ | −157.3 | 7.59/7.57 d(J=1.2Hz) | 1.41/1.40 d(J=1.2/1.0Hz) | 1.18/1.16 d(J=7.6Hz) | 1.04/0.91(d(J=7.0Hz), N(C$_2$H$_5$)$_2$) 2.76–3.09(m, sel., complex) —N(CH$_2$CH$_3$)$_2$ |
| CH(CH$_3$)$_2$ | CH(CH$_3$)$_2$ | −120.4 | 7.61/7.59 d(J=1.2Hz) | 1.37/1.36 d(J=0.9Hz) | 1.18/1.13 d(J=8.5/7.9Hz) | 1.13/1.07/1.04/0.98 d(J=6.7Hz), N[CH(CH$_3$)$_2$]$_2$ |
| CH$_3$ | C$_2$H$_5$ | −134.7/−136.2 | 7.51/7.50 d(J=1.2Hz) | 1.40/1.38 d(J=1.3/0.9Hz) | 1.33/1.31 d(J=8.8Hz) | 3.02/2.86 d(J=3.4Hz), N—CH$_3$ |
| C$_6$H$_5$ | C$_6$H$_5$ | −130.3/128.6 | 7.39/7.47 d(J=1.2Hz) | 1.40/1.36 d(J=1.2/0.9Hz) | 1.15/1.10 d(J=9.8Hz) | |

$^{a)}$relative to 85% H$_3$PO$_4$
$^{b)}$relative to TMS

TABLE 3

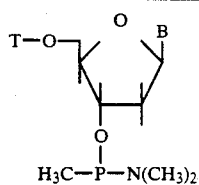

Compounds (IV)

| T[a] | B[b] | 31P-NMR, δ(ppm)[c] 1,2-dichloroethane | 1H-NMR (CDCl₃), δ(ppm)[d] | | | | |
|---|---|---|---|---|---|---|---|
| | | | H-8 | H-2 | OCH₃ | P—N(CH₃)₂ | P—CH₃ |
| MMTr | Ad^Bz | −145.3 | 8.73/8.72 (s) | 8.19/8.16 (s) | 3.76/3.75 (s) | 2.67/2.25 d(J=8.8Hz) | 1.20/1.19 d(J=7.3Hz) |
| DMTr | C^Bz | −146.2/145.8 | | | | | |
| DMTr | G^iBu | −144.8 | | | | | |

[a] MMTr = monomethoxytriphenylmethyl(p-anisoyldiphenylmethyl)
DMTr = dimethoxytriphenylmethyl(di(p-anisoyl)phenylmethyl)
[b] Ad^Bz = 9-(N-6-benzoyladeninyl)
C^Bz = 1-(N-4-benzoylcytosinyl)
G^iBu = 9-(N-2-isobutyroylguaninyl)
[c] relative to 85% H₃PO₄
[d] relative to TMS

TABLE 4

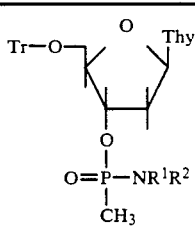

Compounds (VIII)

| R¹=R² | 31P-NMR, δ(ppm)[a] (1,2-dichloroethane) | UV (CH₃OH) λmax (log E) | 1H-NMR(CDCl₃), δ(ppm)[b] | | | |
|---|---|---|---|---|---|---|
| | | | H-6 | P—CH₃ | CH₃ | NR¹R² |
| CH₃ | −40 | 263 nm(3.97) | 7.60/7.50 (d) | 1.38/1.40 d[J=16.2Hz] | 1.41/1.38 | 2.65/2.49 N(CH₃)₂ (d,J=9.5Hz) |
| C₂H₅ | −39.5[c] | 264 nm(4.00) | 7.52 d(1.2Hz) | 1.42 d[J=16.5Hz] | 1.34 d[J=0.9Hz] | 0.94(t, J=7.1Hz) —N(CH₂CH₃)₂ 2.8-3.1m, N(C₂H₅)₂ |
| C₂H₅ | −39.5[d] | 264 nm(3.98) | 7.59 d(J=1.2Hz) | 1.38 d[J=16.5Hz] | 1.36 | 1.07(t, J=7.0Hz) N(C₂H₅)₂ 3.05(dq, J=10.7Hz) J_{CH₂CH₃}=7.0Hz N(C₂H₅)₂ |
| CH(CH₃)₂ | −38 | 264 nm(3.97) | 7.53/7.57 | 1.36 d(J=16.2Hz) | 1.31 | 1.19/1.17/1.04 (d,J=4.0/6.7/6.7Hz) N[CH(CH₃)₂] |
| C₆H₅ | −33.5[c] upper[e] | 260 nm(4.09) | 7.51 (d,J=1.2Hz) | 1.68 d[J=16.8Hz] | 1.28 (s) | |
| C₆H₅ | −30.4[c] lower[e] | 260 nm(4.08) | 7.48 (s) | 1.59 d[J=17.7Hz] | 1.34 (s) | |

[a] relative to 85% H₃PO₄
[b] relative to TMS
[c] ½H₂O
[d] anhydrous
[e] isomers separated, relative mobility in TLC (ethyl acetate/methanol 100:4)

TABLE 5

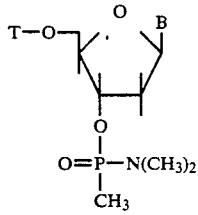

Compounds (VIII)

| T[a] | B[b] | 31P-NMR, δ(ppm)[c] 1,2-dichloroethane | UV (CH₃OH) | 1H-NMR (CDCl₃), δ(ppm)[d] | | | | |
|---|---|---|---|---|---|---|---|---|
| | | | | H-8 | H-2 | O—CH₃ | P—N(CH₃)₂ | P—CH₃ |
| MMTr | Ad^Bz | −41 | 278 nm(4.39) 230 nm(4.52) | 8.73/8.68 (s) | 8.17/8.11 (s) | 3.76/3.75 (s) | 2.66/2.64 d(J=8.9Hz) | 1.23/1.20 d(J=7.4Hz) |

TABLE 5-continued

Compounds (VIII)

[Structure shown: T—O-sugar-B with O=P—N(CH₃)₂ and CH₃ groups]

| T[a] | B[b] | $^{31}$P-NMR, δ(ppm)[c] 1,2-dichloroethane | UV (CH₃OH) | $^{1}$H-NMR (CDCl₃), δ(ppm)[d] H-8 | H-2 | O—CH₃ | P—N(CH₃)₂ | P—CH₃ |
|---|---|---|---|---|---|---|---|---|
| MMTr | C$^{Bz}$ | −41.1 | | | | | | |
| DMTr | G$^{iBu}$ | −41.4 | | | | | | |

[a],[b],[c],[d] as for Table 3

TABLE 6

Compounds (I)

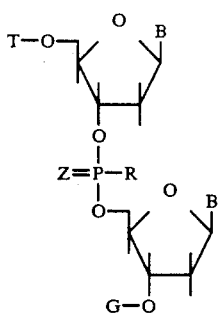

| $^{31}$P-NMR, δ(ppm)[a] | | | $^{1}$H-NMR, CDCl₃, δ(ppm)[c] | | |
|---|---|---|---|---|---|
| X | 1,2-dichloroethane | UV (CH₃OH) λmax (log E) | Zone[b] | —CH₃ | —CH₃ | p-CH₃ |
| S | −99/97.5 | 265 nm(4.25) | upper | 1.89(Tp) (s) | 1.43(pT) (s) | 1.87 d(J=15.2Hz) |
| | | | lower | 1.89(Tp) (s) | 1.46(pT) (s) | 1.80 d(J=15.3Hz) |
| Se | −107.5/−105.5 J37=860Hz p=Se | 264 nm(4.26) | upper | 1.90(Tp) d(J=1.2Hz) | 1.42(pT) d(J=1.1Hz) | 2.04 d(J=14.2Hz) |
| | | | lower | 1.98(Tp) (s) | 1.46(pT) (s) | 1.90 d(J=14.6Hz) |

[a] relative to 85% H₃PO₄
[b] relative mobility in TLC (ethyl acetate/methanol 100:4)
[c] relative to TMS

We claim:

1. A process for the preparation of deoxyribonucleoside phosphonates of the formula I

[Structure I: T—O-sugar-B with Z=P—R linkage to second sugar-B with G—O]

in which
T is a triphenylmethyl protecting group for a primary hydroxyl group;
B is a deoxyribonucleoside base radical, wherein the groups B may be the same or different and are independently selected from the group consisting of 1-thyminyl, 1-(N-4protected)-cytosinyl, 9-(N-6-protected)-adeninyl and 9-(N-2-protected)-quaninyl;
G is an acyl or silyl protecting group for a secondary hydroxyl group;
Z is selected from the group consisting of oxygen, sulfur and selenium; and
R is selected from the group consisting of an alkyl moiety having up to 8 C atoms, cyclohexyl, benzyl, phenyl and phenyl substituted by a member selected from the group consisting of fluorine, chlorine, bromine, lower alkyl, lower alkoxy and trifluoromethyl,
which comprises reacting a difunctional phosphonylating reagent of the formula II

wherein X is chlorine or Y, and Y is a group of the formula

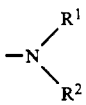

wherein R¹ and R², which are identical or different, are selected from the group consisting of alkyl having up to 8 C atoms and phenyl, or R¹ and R², together with the nitrogen, form a moiety selected from the group consisting of imidazolo, triazolo, nitrotriazolo and tetrazolo moieties, with a nucleoside of the formula III

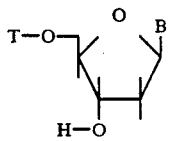 (III)

wherein T and B have the meanings given above, and reacting the resulting compound of the general formula IV

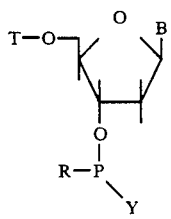 (IV)

with a compound of the formula V

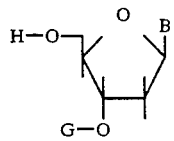 (V)

wherein B and G have the meanings given above, to form compounds of the formula VI

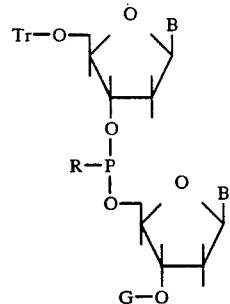 (VI)

wherein T, R, B and G have the meanings given above, and oxidatively converting said compounds of the formula VI to compounds of the formula I, wherein the intermediate products of the process do not spontaneously form significant amounts of symmetrical 3',3'- and 5',5'-products.

2. The process of claim 1, wherein compounds of the formulae II to IV are used in which T is selected from the group consisting of triphenylmethyl, p-anisoyldiphenylmethyl and di(p-anisoyl)phenylmethyl, B is selected from the group consisting of 1-thyminyl, 1-(N-4-benzoylcytosinyl), 9-(N-6-benzoyladeninyl) and 9-(N-2-isobutyroylguaninyl) and R is selected from the group consisting of methyl, ethyl, phenyl and benzyl.

3. The process of claim 1, wherein the compounds of the formula II and III are reacted at −80° to +100° C.

4. The process of claim 3, wherein the reaction takes place at −20° to 0° C.

5. The process of claim 1, wherein the compounds of the formulae IV and V are reacted at −20° to +100° C.

6. The process of claim 5, wherein the reaction is performed at room temperature.

7. The process of claim 1, wherein the compound of the formula VI is oxidatively converted to a compound of the formula I at −80° to +100° C.

8. The process of claim 7, wherein the oxidation is performed at −20° C. to room temperature.

9. A compound of the formula IV

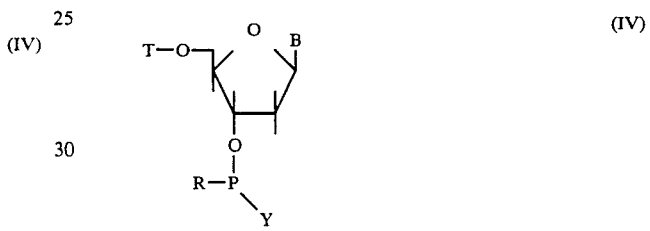 (IV)

in which

T is a triphenylmethyl protecting group for a primary hydroxyl group;

B is a deoxyribonucleoside base radical, wherein the groups B may be the same or different and are independently selected from the group consisting of 1-thyminyl, 1-(N-4-protected-cytosinyl), 9-(N-6-protected)-adeninyl and 9-(N-2-protected)-quaninyl;

R is selected from the group consisting of alkyl having up to 8 C atoms, cyclohexyl, benzyl, phenyl and phenyl substituted by a member selected from the group consisting of fluorine, chlorine, bromine, lower alkyl, lower alkoxy and trifluoromethyl; and Y is a group of the formula

wherein R¹ and R², which are identical or different, are selected from the group consisting of alkyl having up to 8 C atoms and phenyl, or R¹ and R², together with the nitrogen form a moiety selected from the group consisting of imidazolo, triazolo, nitrotriazolo and tetrazolo moieties.

10. The process of claim 1 wherein B is selected from the group consisting of 1-thyminyl, 1-(N-4-acylamino)-cytosinyl, 9-(N-6-acylamino)-adeninyl and 9-(N-2-acylamino)-guaninyl.

11. The process of claim 1 wherein G is selected from the group consisting of benzoyl, acetyl, pivaloyl, and levulonyl groups and t-butyl-dimethylsilyl.

* * * * *